United States Patent [19]

Baschang et al.

[11] Patent Number: 4,959,394
[45] Date of Patent: Sep. 25, 1990

[54] GUANIDINIUM ASPARTATES

[75] Inventors: Gerhard Baschang, Bettingen; Alfred Sallman, Bottmingen, both of Switzerland

[73] Assignee: Ciba-Geigy Corporation, Ardsley, N.Y.

[21] Appl. No.: 437,329

[22] Filed: Nov. 17, 1989

Related U.S. Application Data

[63] Continuation of Ser. No. 353,160, May 15, 1989, abandoned, which is a continuation of Ser. No. 70,290, Jul. 6, 1987, abandoned.

[30] Foreign Application Priority Data

Jul. 11, 1986 [CH] Switzerland .................. 2795/86-1

[51] Int. Cl.$^5$ ............................................ A61K 31/205
[52] U.S. Cl. .................................. 514/555; 514/563; 562/449
[58] Field of Search ................. 562/449; 514/563, 555

[56] References Cited

U.S. PATENT DOCUMENTS

| 4,250,192 | 2/1981 | Sallmann et al. | 424/309 |
| 4,279,926 | 7/1981 | Bruzzese et al. | 260/501.11 |
| 4,440,787 | 4/1984 | de Vincentiis | 260/501.11 |

FOREIGN PATENT DOCUMENTS

| 66458 | 12/1982 | European Pat. Off. |
| 140492 | 5/1985 | European Pat. Off. |

Primary Examiner—James H. Reamer
Attorney, Agent, or Firm—JoAnn Villamizar

[57] ABSTRACT

The L-arginine salt of N-(D)-{[2-(2,6-dichlorophenylamino)phenyl]acetyl]aspartic acid, represented by the formula

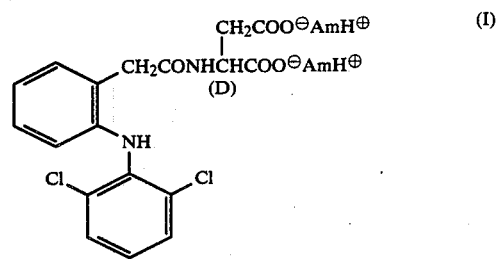

in which AmH $\oplus$ represents the cation derived from L-arginine Am of the formula

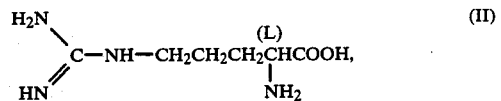

and its hydrates exhibit and excellent water-solubility and a physiologically favorable pH value and also a pleasant taste in aqueous solutions and are therefore excellently suitable for enternal and parenteral forms of administration. It is manufactured by reacting L-arginine with D-{[2-(2,6-dichlorophenylamino)phenyl]-acetyl}aspartic acid.

12 Claims, No Drawings

GUANIDINIUM ASPARTATES

This application is a continuation of application Ser. No. 353,160, filed May 15, 1989 which is a continuation of application Ser. No. 070,290 filed Jul. 6, 1987 now abandoned.

The invention relates to novel guanidinium aspartates, especially the L-arginine salt of N-(D)-{[2-(2,6-dichlorophenylamino)phenyl]acetyl}aspartic acid, represented by the formula

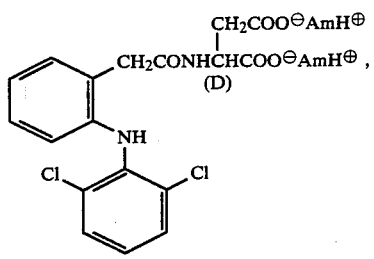

in which AmH ⊕ represents the cation derived from L-arginine Am of the formula

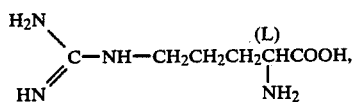

and its hydrates, to a process for the manufacture of the compounds according to the invention, to pharmaceutical preparations containing the latter and to their use.

It is known in the prior art that the D-{[2-(2,6-dichlorophenylamino)phenyl]acetyl}aspartic acid of the formula

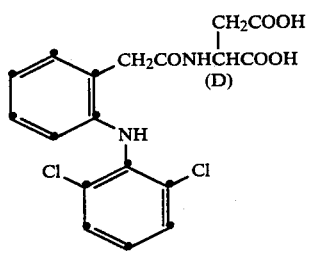

which forms the basis of the compound of the formula I, and its pharmaceutically acceptable salts, that is to say its alkali metal, alkaline earth metal and ammonium salts and also salts with organic bases, have inflammation-inhibiting and analgesic properties while exhibiting comparatively good gastrointestinal tolerability. The prior art, however, describes only D-N-{[2-(2,6-dichlorophenylamino)phenyl]acetyl}aspartic acid and the monosodium salt monohydrate thereof.

The acid of the formula III and its monosodium salt monohydrate have critical disadvantages, however, with regard to their use as an active ingredient in medicaments. The free acid is virtually insoluble in water and therefore is not suitable for all galenical formulations, and especially not for liquid galenical formulations. In addition, it has a bitter taste. The salt is similarly very sparingly soluble in water. Furthermore, its aqueous solution has a physiologically unfavourable pH value and an extremely unpleasant bitter taste, properties that severely limit the use also of the salt as an active ingredient in medicaments. The poor water-solubility and the physiologically unfavourable pH value of the aqueous solution makes it impossible to manufacture liquid forms of administration, such as oral liquid forms of administration, for example syrup or drop formulations, and parenteral liquid forms of administration, for example injection and infusion solutions. In addition, the physiologically unfavourable pH value gives rise to problems of tolerability in the case of administration by means of suppositories, whilst the bitter taste which cannot be masked severely restricts the galenical pharmacist's scope when formulating oral forms of administration and virtually reduces it to providing forms of protective layer, such as capsules, lacquer-coated tablets and the like, with their known disadvantage of a delayed commencement of action.

The invention is based on the surprising discovery that the salt of the formula I is outstandingly watersoluble, and that aqueous solutions thereof have a virtually neutral pH and a pleasant sweet taste. Owing to these surprising properties, the difficulties that still exist with regard to the administration of this group of compounds can be eliminated.

The solubility of the L-arginine salt trihydrate of N-D-{[2-(2,6-dichlorophenylamino)phenyl]acetyl}aspartic acid at 20° C. is approximately 25% by weight and the pH value of a 5.0% by weight aqueous solution is 6.90, whereas the mentioned monosodium salt monohydrate of this acid is water-soluble only by 0.5% by weight and the pH of such a solution has the physiologically unfavourable value of 4.62. Both properties, the greatly improved water-solubility and the virtually neutral pH value of aqueous solutions, of the L-arginine salt provided according to the invention are of great significance with regard to liquid forms of administration, such as those mentioned. The pleasant taste is extremely advantageous for all oral forms of administration.

The L-arginine salt of the formula I has valuable pharmacological properties which virtually correspond to those of the known salt.

In particular, it exhibits a potent inflammationinhibiting action in chronic and sub-chronic inflammation models, such as experimental adjuvant arthritis in rats. In this model, the ED40 for the di-L-arginine salt trihydrate of D-N-{[2-(2,6-dichlorophenylamino)phenyl]-acetyl}aspartic acid is 0.5 mg/kg p.o. . The compound is distinguished, in addition, by an extraordinarily good gastrointestinal tolerability. For example, in an acute ulcer model in rats, no ulcerogenic activity was detected up to the highest tested dose of 160 mg/kg p.o.. In a 10 day ulcer test also, no mortality was observed with a daily dose of 160 mg/kg p.o. . The gastrointestinal blood loss at that dosage was only negligibly increased in comparison with that of control animals.

These results show that the novel salt has a surprisingly wide therapeutic scope which contrasts it favourably with classical inflammation-inhibitors.

The invention relates also to a process, which is based on methods known per se, for the manufacture of guanidinium aspartates of the formula I, characterised in that L-arginine, that is to say the compound of the formula

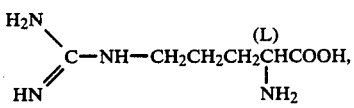

is reacted with N-(D)-{[2-(2,6-dichlorophenylamino)-phenyl]acetyl}aspartic acid of the formula

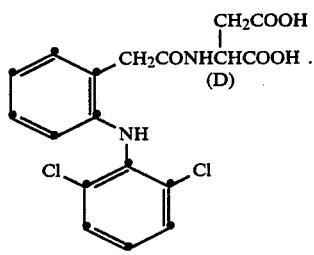

The reaction is effected in customary manner, for example in aqueous or water-containing solution, that is to say in a mixture of water and a water-miscible solvent, such as a lower alkanol or di-lower alkyl ketone, for example methanol, ethanol or acetone. When carrying out the reaction in aqueous solution, the reaction product is advantageously isolated by lyophilisation (a form of freeze-drying).

The invention relates also to the use of the compound of salt-like composition of the formula I as a pharmacological, especially inflammation-inhibiting, agent for the treatment of chronic and sub-chronic inflammatory diseases, such as inflammations of a traumatic and/or degenerative aetiology, for example arthritis and polyarthritis. It can be used, preferably in the form of pharmaceutical preparations, in a method for the therapeutic treatment of the animal body or the human body, especially for the treatment of chronic and sub-chronic inflammatory conditions, such as arthritic syndromes.

The dosage of the active ingredient, which may be administered on its own or together with the customary carrier and adjunct, depends on the species to be treated, its age and individual condition, and on the method of administration. Depending on the nature of the disease, individual condition and age, the daily doses, for example for warm-blooded animals weighing approximately 70 kg, are preferably approximately from 100 to 500 mg, especially from approximately 200 mg to approximately 500 mg, and more especially from approximately 250 mg to approximately 400 mg.

The invention relates furthermore to pharmaceutical preparations containing the compound of the formula I as active ingredient, and to processes for the manufacture thereof.

The pharmaceutical preparations according to the invention are for parenteral or enteral, such as peroral or rectal, administration, and also for sub-lingual administration, to warm-blooded animals. They contain preferably from approximately 20 mg to approximately 200 mg, especially from approximately 50 mg to approximately 150 mg, of a compound of the formula I together with pharmaceutically acceptable carriers.

Owing to the excellent water-solubility of the salt-type compound of the formula I, there are suitable for parenteral administration especially aqueous solutions, which are provided, for example, in dosage unit form, such as ampoules or phials. Aqueous solutions contain, for example, approximately from 1.0%, preferably 2.0% (g/100 ml), up to saturation, especially up to approximately 20.0%, preferably 10.0% (g/100 ml), active ingredient.

Suitable for oral administration are, for example, solid forms of administration, preferably those in dosage unit form, such as tablets, also lacquer-coated tablets or capsules, for example gelatine dry-filled capsules or sealed gelatine capsules, above all, however, formulations that can be dissolved to form liquid oral forms of administration, such as water-soluble powders and effervescent powders, preferably in single dose sachets, effervescent tablets or reconstitutable dry syrups, and liquid oral forms of administration, such as drops, mixtures, juices, syrups, elixirs and the like, and, for rectal administration, for example suppositories. Solid forms of administration contain approximately from 2% to 80% by weight, tablets and lacquer-coated tablets, for example approximately from 10% to 60% by weight, capsules, for example approximately from 20% to 80% by weight, and suppositories, for example approximately from 2% to 25% by weight, active ingredient. Liquid oral forms of administration contain, for example, approximately from 1.0%, preferably 2.0% (g/100 ml), up to saturation, especially up to approximately 20.0%, preferably 10.0% (g/100 ml), active ingredient.

The pharmaceutical preparations according to the invention can be manufactured in a manner known per se by mixing the active ingredient component with customary pharmaceutical adjuncts.

For parenteral administration by injection or infusion there are suitable, as mentioned, especially isotonic aqueous solutions which may contain, in addition to additives for regulating the osmotic pressure, such as sodium chloride, stabilising agents, such as heavy metal complex formers, anti-oxidants and/or buffer solutions.

Orally administrable solid forms of administration, such as those mentioned, can be manufactured by conventional mixing, granulating or confectioning methods. For example, the active ingredients can be mixed with solid carriers, a resulting mixture can be granulated, and the mixture or granulate can be processed to form tablets or dragée cores, if desired or necessary after the addition of suitable adjuncts. Suitable carriers are especially fillers, such as sugars, for example lactose, saccharose, mannitol or sorbitol, cellulose preparations and/or calcium phosphates, for example tricalcium phosphate or calcium hydrogen phosphate, binders, such as starch pastes based on, for example, corn, wheat, rice or potato starch, gelatine, methylcellulose, hydroxypropylmethylcellulose, hydroxypropylcellulose, and/or polyvinylpyrrolidone, and/or, if desired, disintegrators, such as the mentioned starches, also carboxymethyl starch, crosslinked polyvinylpyrrolidone, agar, alginic acid or a salt thereof, such as sodium alginate, or low molecular weight carboxymethylcellulose. Adjuncts are especially flow-regulating agents and lubricants, for example silica, talc, stearic acid or salts thereof, such as magnesium or calcium stearate, and/or polyethylene glycol.

Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or aqueous dispersions of ethyl acrylate/-methyl methacrylate copolymers. For the manufacture of coatings that are resistant to gastric juices, solutions of suitable cellulose preparations, such as acetylcellulose phthalate or hydroxypropylmethylcellulose phthalate, or aqueous dispersions of, for example, methacrylic acid/methacrylate copolymers are used. Colourings or pigments can be added to the tablets or coatings, for example for identification purposes or to indicate different doses of active ingredient.

Dry-filled capsules consisting of gelatine and also soft, sealed capsules consisting of gelatine and a plasticiser, such as glycerine or sorbitol, may contain the active ingredient in the form of a powder or granulate, for example in admixture with fillers, such as cellulose or lactose, binders, such as starches, and/or glidants, such as talc or magnesium stearate, and, if necessary, customary stabilisers. In soft capsules, the active ingredient is preferably dissolved or suspended in suitable liquids, such as fatty oils, paraffin oil or liquid polyethylene glycols, it being possible to add also stabilisers.

Formulations that can be dissolved to form liquid oral forms of administration, such as water-soluble powders and effervescent powders, preferably in single dose sachets, effervescent tablets or reconstitutable dry syrups, are based on the reaction of a pharmaceutically acceptable organic acid with an alkali metal or alkaline earth metal carbonate compound, in which carbon dioxide is liberated. Pharmaceutically acceptable organic acids that come into consideration are, for example, citric acid, tartaric acid, fumaric acid, maleic acid, ascorbic acid and similar aliphatic dicarboxylic acids which are optionally hydroxylated, and alkali metal and alkaline earth metal carbonate compounds that come into consideration are, for example, sodium hydrogen carbonate, sodium carbonate, calcium or magnesium carbonate or calcium hydrogen carbonate. Other galenical constituents correspond substantially to those of tablets. In addition, colourings and/or flavourings and also preservatives are customarily added.

Liquid oral forms of administration, such as drops, mixtures and juices, are, in accordance with their physical form, preferably solutions, but may also be in the form of reconstitutable solids, such as dry syrups.

Solutions are preparations that are obtained by dissolving the active ingredient in water or in a suitable water-containing solvent mixture.

Syrups are viscous aqueous or water-containing solutions that contain sugars or sugar alcohols (for example sorbitol) in high concentration.

Elixirs are aqueous-alcoholic sweetened solutions. Their high content of ethanol and other solvents, such as glycols, makes it possible to administer sparingly water-soluble active ingredients in the form of clear solutions.

Dry syrups are preparations that contain all the constituents of the finished preparation in the form of a powder or granulate so that, before use, it is necessary only to add the required amount of water in order to dissolve them. The reconstituted syrup remains stable during the consumption period specified by the manufacturer.

The liquid forms of administration mentioned may be sweetened, flavoured and/or coloured.

Suppositories consisting of a combination of the active ingredient with a suppository base material are suitable, for example natural or synthetic glycerol esters, paraffin hydrocarbons, polyethylene glycols or higher alkanols or mixtures thereof. It is also possible to use gelatine rectal capsules which contain a combination of the active ingredient with a base material; suitable base materials are, for example, liquid triglycerides, polyethylene glycols or paraffin hydrocarbons together with suspension stabilisers, such as waxes and other swelling agents.

The following Examples serve merely to illustrate the invention and are not intended to limit it in any way. Temperatures are given in degrees Celsius.

EXAMPLE 1

55.0 g of D-N-{[2-(2,6-dichlorophenylamino)phenyl]acetyl}aspartic acid are added to a solution of 46.64 g of L-arginine in 300 ml of water while stirring at room temperature. The whole is then stirred for 30 minutes, and the clear solution is frozen in an acetone/dry ice bath and subsequently lyophilised. The residue, the L-arginine salt trihydrate of D-{[2-(2,6-dichlorophenylamino)phenyl]acetyl}aspartic acid, is a white, amorphous powder of m.p. 155°–165° (with decomposition); solubility: 25% by weight in water at 20° C.

EXAMPLE 2

An injection solution in dosage unit form, containing 150 mg of the L-arginine salt trihydrate of N-(D)-{[2-(2,6-dichlorophenylamino)phenyl]acetyl}-aspartic acid as active ingredient, can be manufactured, for example, in the following manner:

| Composition: (for 1000 dosage units) | |
| --- | --- |
| active ingredient | 150.00 g |
| sodium chloride | 22.50 g |
| water to | 2500.00 ml |

The active ingredient is introduced into 1250 ml of water and dissolved while stirring vigorously. The mixture is filtered through a micro-filter, diluted, while stirring, with a solution of 22.5 g of sodium chloride in 1000.0 ml of water, made up with water to 2500 ml and sealed under sterile conditions in glass ampoules each containing 2.50 ml of the solution.

EXAMPLE 3

Tablets, each containing 380 mg of the L-arginine salt trihydrate of N-(D)-{[2-(2,6-dichlorophenylamino)phenyl]acetyl}aspartic acid as active ingredient, can be manufactured as follows:

| Composition: (for 1000 tablets) | |
| --- | --- |
| active ingredient | 380.00 g |
| lactose | 25.00 g |
| corn starch | 5.00 g |
| talc | 5.50 g |
| calcium stearate | 1.50 g |
| water | q.s. |
| methylene chloride | q.s. |

The active ingredient, the lactose and 40 g of the corn starch are mixed, moistened with a paste prepared from 15 g of corn starch and water (while heating) and granulated. The granulate is dried, and the remainder of the corn starch, the talc and the calcium stearate are added and mixed with the granulate. The mixture is compressed to form tablets (weight: 400 mg). Weight of a lacquer-coated tablet: approximately 415 mg.

EXAMPLE 4

Tablets, each containing 50 mg of the L-arginine salt trihydrate of N-(D)-{[2-(2,6-dichlorophenylamino)-phenyl]acetyl}aspartic acid as active ingredient, can be manufactured as follows:

| Composition: (for 1000 tablets) | |
|---|---|
| active ingredient | 50.0 g |
| lactose | 155.0 g |
| potato starch | 150.0 g |
| gelatine | 25.0 g |
| talc | 50.0 g |
| magnesium stearate | 15.0 g |
| silica (highly disperse) | 10.0 g |
| ethanol | q.s. |

The active ingredient is mixed with the lactose and 292 g of the potato starch, and the mixture is moistened with an alcoholic solution of the gelatine and granulated through a sieve. After drying, the remainder of the potato starch, the talc, the magnesium stearate and the highly disperse silica are mixed in and the mixture is compressed to form tablets each weighing 600 mg and having the active ingredient content mentioned above, which may, if desired, be provided with dividing notches for finer adjustment of the dosage.

EXAMPLE 5

Lacquer-coated tablets, each containing 100 mg of the L-arginine salt trihydrate of N-(D)-{[2-(2,6-dichlorophenylamino)phenyl]acetyl}aspartic acid as active ingredient, can be manufactured as follows:

| Composition: (for 1000 tablets) | |
|---|---|
| active ingredient | 100.00 g |
| lactose | 90.00 g |
| corn starch | 50.00 g |
| talc | 7.50 g |
| calcium stearate | 3.50 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, moistened with a paste prepared from 15 g of corn starch and water (while heating) and granulated. The granulate is dried, and the remainder of the corn starch, the talc and the calcium stearate are added and mixed with the granulate. The mixture is compressed to form tablets (weight: 280 mg) and these are coated with a solution of the hydroxypropylmethylcellulose and the shellac in methylene chloride; final weight of a lacquer-coated tablet: 300 mg.

EXAMPLE 6

Gelatine dry-filled capsules, each containing 350 mg of the L-arginine salt trihydrate of N-(D)-{[2-(2,6-dichlorophenylamino)phenyl]acetyl}-aspartic acid as active ingredient, can be manufactured as follows:

| Composition: (for 1000 capsules) | |
|---|---|
| active ingredient | 350.00 g |
| microcrystalline cellulose | 30.00 g |
| sodium lauryl sulphate | 2.00 g |
| magnesium stearate | 8.00 g |

The sodium lauryl sulphate is added to the active ingredient (lyophilised) by sieving through a sieve having a mesh width of 0.2 mm and the two components are intimately mixed for 10 minutes. The microcrystalline cellulose is then sieved in through a sieve having a mesh width of 0.9 mm and the whole is again intimately mixed for 10 minutes. Finally, the magnesium stearate is sieved in through a sieve having a mesh width of 0.8 mm and, after further mixing for 3 minutes, the mixture is introduced into gelatine dry-filled capsules of size 0 (elongated) in portions of 390 mg in each case.

EXAMPLE 7

Effervescent tablets, each containing 100 mg of the L-arginine salt trihydrate of N-(D)-{[2-(2,6-dichlorophenylamino)phenyl]acetyl}aspartic acid as active ingredient, can be manufactured as follows:

| Composition: (for 1000 units) | |
|---|---|
| active ingredient | 100.00 g |
| citric acid, anhydrous | 500.00 g |
| sodium hydrogen carbonate, granular | 525.00 g |
| sodium carbonate, anhydrous | 375.00 g |
| orange flavouring, natural | 5.00 g |
| sodium benzoate | 95.00 g |

The components are intimately ground and compressed in a high-pressure tablet press to form tablets each weighing 1.6 g.

EXAMPLE 8

Single dose sachets, each containing 100 mg of the L-arginine salt trihydrate of N-(D)-{[2-(2,6-dichlorophenylamino)phenyl]acetyl}aspartic acid as active ingredient, can be manufactured as follows:

| Composition: (for 1000 units) | |
|---|---|
| active ingredient | 100.00 g |
| citric acid, anhydrous | 140.00 g |
| lemon juice, freeze-dried | 90.00 g |
| lemon flavourings, natural | 1.00 g |
| sodium carbonate | 30.00 g |
| sodium hydrogen carbonate | 55.00 g |
| sodium saccharin | 5.00 g |

The components are introduced, optionally after being granulated with ethanol, into polyethylene sachets each containing 0.65 g of the formulation.

We claim:

1. The L-arginine salt of N-(D [2-(2,6-dichlorophenylamino)phenyl]acetyl}aspartic acid, of the formula

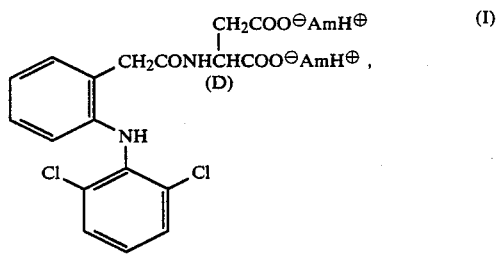

in which AmH $\oplus$ represents the cation of L-arginine Am of the formula

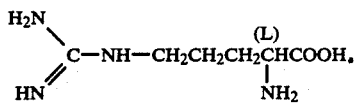

2. A compound claimed in claim 1 being N-(D)-}[2-(2,6dichlorophenylamino)phenyl]acetyl}-aspartic acid L-arginine salt in the form of the trihydrate.

3. Pharmaceutical preparations containing a compound according to claim 1 together with pharmaceutically acceptable adjuncts.

4. Pharmaceutical preparations according to claim 3 in liquid form for parenteral administration, comprising injection solutions or infusion solutions.

5. Pharmaceutical preparations according to claim 3 for enteral administration comprising solid or liquid oral, and solid rectal forms of administration.

6. Pharmaceutical preparations according to claim 3 in liquid administration form for oral administration, comprising drops, mixtures, juices, elixirs syrups and 7. Pharmaceutical preparations according to claim 3 in a solid form that can be dissolved to form liquid oral forms of administration comprising water-soluble powders, effervescent powders, effervescent tablets and reconstitutable dry syrups.

8. Pharmaceutical preparations according to claim 3 in the form of water-soluble powders, effervescent tablets or reconstitutable dry syrups.

9. Pharmaceutical preparations in the form of aqueous solutions according to claim 3.

10. Pharmaceutical preparations according to claim 3 in solid administration form for oral or rectal administration comprising lacquer-coated tablets or capsules and suppositories.

11. A method for the treatment of inflammatory diseases in animals comprising administering to a patient in need thereof an antiinflammatory effective amount of a compound according to claim 1.

12. Pharmaceutical preparations according to claim 7 in the form of single dose sachets.

* * * * *